US009301912B2

(12) United States Patent
Tournilhac et al.

(10) Patent No.: US 9,301,912 B2
(45) Date of Patent: Apr. 5, 2016

(54) MATERIAL FORMED FROM DENDRITIC MOLECULES CONTAINING ASSOCIATIVE GROUPS

(71) Applicants: ARKEMA FRANCE, Colombes (FR); Centre National De La Recherche Scientifique CNRS, Paris (FR)

(72) Inventors: François-Genes Tournilhac, Paris (FR); Manuel Hidalgo, Brignais (FR); Ludwik Leibler, Paris (FR)

(73) Assignees: Arkema France, Colombes (FR); Centre National De La Recherche Scientifique CNRS, Paris (FR)

( * ) Notice: Subject to any disclaimer, the term of this patent is extended or adjusted under 35 U.S.C. 154(b) by 0 days.

(21) Appl. No.: 14/592,461

(22) Filed: Jan. 8, 2015

(65) Prior Publication Data
US 2015/0132239 A1    May 14, 2015

Related U.S. Application Data

(63) Continuation of application No. 12/746,484, filed as application No. PCT/EP2008/066652 on Dec. 2, 2008, now abandoned.

(30) Foreign Application Priority Data

Dec. 6, 2007    (FR) ...................... 07 08516

(51) Int. Cl.
| | |
|---|---|
| *A61K 8/85* | (2006.01) |
| *A61Q 1/00* | (2006.01) |
| *A61Q 3/00* | (2006.01) |
| *A61Q 5/00* | (2006.01) |
| *C07D 249/12* | (2006.01) |
| *C08G 59/22* | (2006.01) |
| *C08G 59/42* | (2006.01) |
| *C08G 63/12* | (2006.01) |
| *C08G 63/685* | (2006.01) |
| *C07D 233/36* | (2006.01) |
| *C07D 233/40* | (2006.01) |
| *C07D 251/02* | (2006.01) |
| *C07D 253/02* | (2006.01) |
| *A61Q 5/06* | (2006.01) |
| *C07D 249/14* | (2006.01) |
| *A61K 8/49* | (2006.01) |
| *A61K 8/88* | (2006.01) |
| *A61Q 5/02* | (2006.01) |
| *A61Q 19/00* | (2006.01) |
| *C08G 83/00* | (2006.01) |
| *A61K 8/84* | (2006.01) |
| *C08G 59/02* | (2006.01) |
| *A61Q 1/02* | (2006.01) |
| *A61Q 5/12* | (2006.01) |

(52) U.S. Cl.
CPC . *A61K 8/85* (2013.01); *A61K 8/496* (2013.01); *A61K 8/4946* (2013.01); *A61K 8/4966* (2013.01); *A61K 8/84* (2013.01); *A61K 8/88* (2013.01); *A61Q 5/02* (2013.01); *A61Q 19/00* (2013.01); *C07D 233/36* (2013.01); *C07D 233/40* (2013.01); *C07D 249/12* (2013.01); *C07D 249/14* (2013.01); *C07D 251/02* (2013.01); *C07D 253/02* (2013.01); *C08G 59/02* (2013.01); *C08G 59/22* (2013.01); *C08G 59/42* (2013.01); *C08G 63/12* (2013.01); *C08G 63/685* (2013.01); *C08G 63/6854* (2013.01); *C08G 83/003* (2013.01); *A61K 2800/544* (2013.01); *A61Q 1/02* (2013.01); *A61Q 5/06* (2013.01); *A61Q 5/12* (2013.01)

(58) Field of Classification Search
IPC ................... C08G 59/22,59/42, 63/12, 63/685, C08G 63/6854; C07D 233/36, 233/40, 249/12, C07D 249/14, 251/02, 253/02; A61K 8/85, A61K 2800/544, 8/4946, 8/496, 8/4966; A61Q 5/02, 19/00
See application file for complete search history.

(56) References Cited

U.S. PATENT DOCUMENTS

| | | | | |
|---|---|---|---|---|
| 5,196,502 | A  * | 3/1993 | Turner et al. ................... | 528/272 |
| 8,530,671 | B2 * | 9/2013 | Tournilhac et al. ......... | 548/324.5 |
| 8,629,213 | B2 * | 1/2014 | Hidalgo et al. ................ | 525/189 |
| 8,889,771 | B2 * | 11/2014 | Dufaure et al. ............... | 524/106 |
| 8,975,363 | B2 * | 3/2015 | Hidalgo et al. ............. | 528/339.3 |
| 2007/0123694 | A1* | 5/2007 | Tournilhac et al. ........... | 528/422 |

(Continued)

FOREIGN PATENT DOCUMENTS

| | | | |
|---|---|---|---|
| JP | 2007292946 | * | 11/2007 |
| JP | 2007292946 | A | 11/2007 |

(Continued)

OTHER PUBLICATIONS

Office Action related to corresponding Japanese Patent Application No. 2010-536429 dated Sep. 17, 2013.

*Primary Examiner* — Rabon Sergent
(74) *Attorney, Agent, or Firm* — Millen, White, Zelano & Branigan, P.C.

(57) ABSTRACT

The present invention relates to a material comprising dendritic molecules each constituted of fragments that are at least bifunctional and of fragments that are at least trifunctional joined together by ester or thioester bridges, alone or in combination with amide or urea bridges, said bridges being formed from two functions carried by different fragments, said molecules containing, on the fragments located at the ends of the dendritic branches, associative end groups capable of forming associations with one another by hydrogen bonds and joined covalently to the functions that are not involved in said bridges. It also relates to the method of production thereof, as well as to its uses and to compositions, notably cosmetic, containing this material.

22 Claims, No Drawings

(56) References Cited

U.S. PATENT DOCUMENTS

| | | | |
|---|---|---|---|
| 2008/0221272 A1* | 9/2008 | Tournilhac et al. | 525/194 |
| 2009/0062551 A1* | 3/2009 | Tournilhac et al. | 548/313.7 |
| 2010/0135940 A1* | 6/2010 | Grimaldi et al. | 424/62 |
| 2010/0286357 A1* | 11/2010 | Matsumura et al. | 528/59 |

FOREIGN PATENT DOCUMENTS

| | | | |
|---|---|---|---|
| WO | 9311200 A1 | | 6/1993 |
| WO | WO 93/11200 | * | 6/1993 |
| WO | 9317060 A1 | | 9/1993 |
| WO | WO 9317060 | * | 9/1993 |
| WO | 9607688 A1 | | 3/1996 |
| WO | WO 9607688 | * | 3/1996 |
| WO | 03059964 A2 | | 7/2003 |
| WO | WO 03059964 | * | 7/2003 |
| WO | 2006016041 A1 | | 2/2006 |
| WO | WO 2006016041 | * | 2/2006 |
| WO | 2006087475 A1 | | 8/2006 |
| WO | WO 2006087475 | * | 8/2006 |
| WO | 2008029065 A2 | | 3/2008 |
| WO | WO 2008029065 | * | 3/2008 |
| WO | 2009/071554 A1 | | 6/2009 |
| WO | WO 2009/071554 | * | 6/2009 |

* cited by examiner

MATERIAL FORMED FROM DENDRITIC MOLECULES CONTAINING ASSOCIATIVE GROUPS

The present invention relates to novel supramolecular materials.

The so-called supramolecular materials are materials constituted of compounds linked together by noncovalent bonds, such as hydrogen bonds, ionic and/or hydrophobic bonds. One advantage of these materials is that these physical bonds are reversible, notably under the influence of temperature or by the action of a selective solvent. It is thus possible to envisage using them in fields of application such as coatings (paints, cosmetics etc.), adhesives, hot-melt glues and powder paints.

Some of them additionally possess elastomeric properties. In contrast to the classical elastomers, these materials have the advantage of being able to become fluid above a certain temperature, which facilitates their application, notably good mould filling, as well as their recycling. Although they are not constituted of crosslinked polymers but of small molecules, those materials are, like the elastomers, capable of displaying dimensional stability for very long periods and of recovering their initial shape after considerable deformation. They can be used for making seals, thermal or acoustic insulation, tyres, cables, cladding, soles of footwear, packaging, patches (cosmetic or dermo-pharmaceutical), wound dressings, flexible hose clips, vacuum tubes, pipes and hoses for conveying fluids.

Supramolecular materials have already been described by the applicant.

Thus, document WO 03/059964 describes a supramolecular material obtained by reacting urea with polyalkylene imines, polyamines or polyamides having in common that they contain free primary or secondary amine functions. The prepolymer obtained can notably have imidazolidone functions and free primary or secondary amine functions which are then able to react with an alkyl halide. The polyamides can themselves be obtained by condensation of polyamines on dimers and trimers of fatty acids. This material does not display elastomeric properties.

Moreover, document WO 2006/016041 discloses a supramolecular material, obtained by grafting compounds bearing an its imidazolidone group, such as N-aminoethyl-2-imidazolidone (UDETA) onto a polymer such as a PMMA, which contains anhydride functions.

Yet other supramolecular materials are described in application WO 2008/029065. They can be obtained by reaction of diners and/or trimers of fatty acids with compounds containing associative groups.

Moreover, an elastomeric supramolecular material is disclosed in document WO 2006/087475. It comprises molecules containing at least three associative functional groups, such as imidazolidone groups, which are able to form several physical bonds and can be obtained by reacting urea with the product of the reaction of a polyamine with triacids.

The drawback of these materials is that their method of preparation requires the use of urea, which leads to release of ammonia. Moreover, to obtain an elastomeric material such as described in application WO 2006/087475, there must be close control of the operating conditions such as the purity of the reactants, their order of introduction, the duration and temperature of the reactions, as well as the homogeneity of the mixture. In particular, the oligoamidoamine derived from fatty acid obtained by polycondensation of a polyamine such as diethylene triamine, DETA, or triethylene tetramine, TETA, and of a fatty acid must meet criteria that are very specific in terms of purity and degree of polycondensation to yield an elastomer.

The applicant has now developed novel supramolecular materials that can be obtained by a method that is easy to apply and does not lead to release of ammonia, in contrast to the methods using urea as a reactant. In contrast to those described in the above documents, these materials contain molecules having a particular dendritic structure that can endow them with very varied properties depending on the proportions of the reactants used for their synthesis. Thus, depending on the number of reactive functions present in the starting compounds and the number of reactive functions remaining at the end of the first stage of synthesis, numbers that can easily be adjusted by the choice of starting materials and by using an appropriate stoichiometric ratio, we can obtain by choice and in a controlled manner, a semi-crystalline or amorphous solid, a viscoelastic liquid or an elastomeric material, optionally thermoplastic. More precisely, when the average functionality of the monomers is not very high, essentially linear molecules are produced having viscoelastic behaviour end which can optionally have a semi-crystalline or amorphous solid phase, whereas networks optionally containing an insoluble fraction and displaying elastomeric properties form when this functionality is high. It is also possible to obtain materials offering a compromise of properties such as capacity for self-repair/creep resistance or of fluidity/resistance to tearing.

It is thus notably possible to obtain a material having the properties of a thermoplastic elastomer, i.e. of a material capable, at room temperature, of undergoing uniaxial deformation, advantageously of at least 20% for 15 minutes, then of recovering its initial dimension once the stress is removed, with a permanent strain less than 5% of its initial dimension, and which can be formed or reformed at high temperature. It has moreover been observed that this material could be self-healing, i.e. capable, once cut, torn or scratched, of repairing itself simply by bringing the fractured surfaces back into contact without requiring heating or the application of considerable pressure or of carrying out any chemical reaction, the material thus repaired still having elastomeric properties.

The material according to the invention can be obtained by a method comprising reacting, in a first stage, a first compound containing a high proportion of molecules that are at least trifunctional with a second compound that contains one or more associative groups, in non-stoichiometric proportions allowing free functions to remain on the first compound, to obtain a material that is reacted, in a second stage, with a compound that is at least bifunctional.

Document, WO 93/11200 describes a crosslinkable hot-melt adhesive comprising a system with two components A and B, comprising respectively a constituent (Ab), such as a polyamide with free amine functions, which can be crosslinked by reaction with the epoxy functions of a constituent (Bb). The polyamide itself can be obtained by reaction of a mixture of monomeric and dimeric fatty acids with a compound containing at least two primary amino groups. As a variant, constituent (Ab) can be an aminoalkylimidazolidone. A possible example of constituent (Bb) is diglycidyl ether of bisphenol A (DGEBA). It is not, however, envisaged that compound (Ab) could be an amide obtained from trimeric fatty acids and an aminoalkylimidazolidone, so that this method does not make it possible to obtain the particular dendritic molecules constituting the material according to the invention.

The present invention therefore relates to a material comprising dendritic molecules, each constituted of fragments that are at least bifunctional and of fragments that are at least trifunctional, joined together by ester or thioester bridges, alone or in combination with amide or urea bridges, said bridges being formed from two functions carried by different fragments, said molecules containing, moreover, on the fragments located at the ends of the dendritic branches, associative end groups capable of forming associations with one another by hydrogen bonds and joined covalently to the functions that are not participating in said bridges.

According to a preferred embodiment of the invention, this material can be obtained according to the method comprising the following successive stages:

(a) reaction of at least one compound that is at least trifunctional (A) bearing first and second functions with at least one compound (B) containing, on the one hand, at least one reactive group capable of reacting with the first functions of (A) and, on the other hand, at least one associative group;

(b) reaction of the compound or compounds obtained in stage (a) with at least one compound that is at least bifunctional (C), whose functions are capable of reacting with the second functions of compound (A) to form ester or thioester bridges, alone or in combination with amide or urea bridges.

The invention therefore also relates to this method, as well as the material that can thus be obtained.

By "dendritic", we mean, according to the invention, a tree-like or branched molecule whose backbone has at least two branchings. This definition does not exclude the possibility of several branchings of the same molecule joining together to form loops.

It is possible for a fraction of the dendritic molecules according to the invention to be insoluble both in water and in any organic solvent.

By "associative groups", we mean groups that are able to form associations with one another by hydrogen bonds, advantageously by 1 to 6 hydrogen bonds. Examples of associative groups that can be used according to the invention are the imidazolidonyl, triazolyl, triazinyl, bis-ureyl, and ureidopyrimidyl groups. The average number of associative end groups per molecule of the material is preferably at least 3. It is advantageously at most 6. The latter are joined covalently to the molecule. By "covalently", we mean that the associative groups are connected to the end functions of the molecule either via a direct bond or, preferably, via a chain, notably alkylene.

By "reactive groups" or "functions", we mean chemical functions that are able to react with other chemical functions to form covalent bonds, leading notably to the formation of ester, thioester, amide, urea or urethane bridges and in particular ester and amide bridges. A "bifunctional" compound denotes a compound bearing two reactive functions, which may be identical or different. An "at least trifunctional" compound denotes a compound bearing at least three reactive functions, which may be identical or different.

By "fragment", we mean, in the sense of the invention, a unit of a molecule located between two or three bridges as defined above. A "bifunctional" fragment is one that can be obtained from a bifunctional compound and a "trifunctional" fragment is one than can be obtained from a trifunctional compound. The dendritic molecules according to the invention contain fragments that are at least bifunctional, advantageously bifunctional, and fragments that are at least trifunctional, advantageously trifunctional.

Compound (A) employed in the first stage of the method according to the invention can in particular have at least three identical or different functions selected from the acid, ester or acyl chloride functions. It contains advantageously from 5 to 100, preferably from 12 to 100 and more preferably from 24 to 90 carbon atoms.

Compound (A) can, in the first stage of the method according to the invention, be mixed with mono- and bifunctional compounds, such as mono- and diacids, in particular monomers and dimers of fatty acids.

It is preferable to use trimers (oligomers of 3 identical or different monomers) and mixtures of dimers and trimers of fatty acids of vegetable origin. These compounds result from the oligomerization of unsaturated fatty acids such as: undecylenic, myristoleic, palmitoleic, oleic, linoleic, linolenic, ricinoleic, eicosenoic, docosenoic acid, that are usually found in pine oils (tall oil fatty acids), colza oil, maize oil, sunflower oil, soya oil, grapeseed oil, linseed oil, jojoba oil, as well as the eicosapentaenoic and docosahexaenoic acids that are found in fish oils.

As examples of trimers of fatty acids, we may mention the compounds of the following formulae which illustrate the cyclic trimers obtained from fatty acids with 18 carbon atoms, knowing that the commercially available compounds are mixtures of steric isomers and positional isomers of these structures, optionally partially or fully hydrogenated.

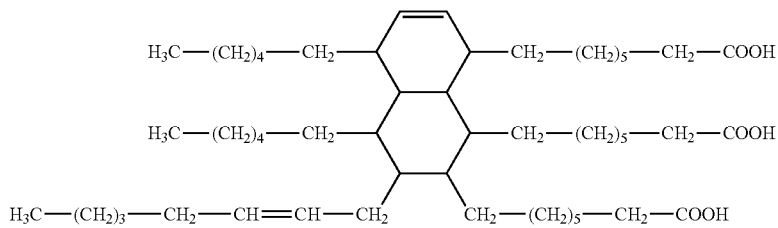

Trimer of C18 Acid

We can thus use a mixture of oligomers of fatty acids containing dimers, trimers and monomers of linear or cyclic $C_{18}$ fatty acids, said mixture being mainly of dimers and trimers and containing a small percentage (usually less than 5%) of monomers. Preferably, said mixture comprises:

0.1 to 40 wt. %, preferably 0.1 to 5 wt. % of monomers of identical or different fatty acids, 0.1 to 99 wt. %, preferably 18 to 85 wt. % of dimers of identical or different fatty acids, and 0.1 to 90 wt. %, preferably 5 to 85 wt. %, of trimers of identical or different fatty acids.

We may mention, as examples of dimer/trimer mixtures of fatty acids (wt. %):

Pripol® 1017 from Uniqema, mixture of 75-80% of dimers and 18-22% of trimers with around 1-3% of monomeric fatty acids, Pripol® 1048 from Uniqema, mixture of 50/50% of dimers/trimers, Pripol® 1013 from Uniqema, mixture of 95-98% of dimers and 2-4% of trimers with max. 0.2% of monomeric fatty acids, Pripol® 1006 from Uniqema, mixture of 92-98% of dimers and a maximum of 4% of trimers with max. 0.4% of monomeric fatty acids, Pripol® 1040 from Uniqema, mixture of dimers and trimers of fatty acid with at least 75% of trimers and less than 1% of monomeric fatty acids, Unidyme® 60 from Arizona Chemicals, mixture of 33% of dimers and 67% of trimers with less than 1% of monomeric fatty acids, Unidyme® 40 from Arizona Chemicals, mixture of 65% of dimers and 35% of trimers with less than 1% of monomeric fatty acids, Unidyme® 14 from Arizona Chemicals, mixture of 94% of dimers and less than 5% of trimers and other higher oligomers with of the order of 1% of monomeric fatty acids, Empol® 1008 from Cognis, mixture of 92% of dimers and 3% of higher oligomers, essentially of the trimers, with of the order of 5% of monomeric fatty acids, Empol® 1018 from Cognis, mixture of 81% of dimers and 14% of higher oligomers, being essentially trimers, with of the order of 5% of monomeric fatty acids, Radiacid® 0980 from Oleon, mixture of dimers and trimers with at least 70% of trimers.

The products Pripol®, Unidyme®, Empol®, and Radiacid® contain monomers of $C_{18}$ fatty acids and oligomers of fatty acids corresponding to multiples of $C_{18}$.

According to a variant of the invention, instead of triacids we can use, as compound (A), a compound containing at least three ester or acyl chloride functions.

As an example of ester, we may mention a methyl, ethyl or isopropyl ester (preferably methyl) of a trimer of fatty acid or of a mixture of oligomers of fatty acids as defined above.

In another variant, compound (A) can be a compound that is at least trifunctional containing at least two different functions, advantageously selected from the acid, ester and acyl chloride functions.

For its part, compound (B) contains at least one reactive group, which notably can be selected from the primary or secondary amine or alcohol groups. As a variant, compound (B) can contain at least two such groups, which may be identical, or different.

Notably in the case when the reactive group of compound (B) is able to react simultaneously with the first and second functions of compound (A), it is preferable, in the first stage of the method according to the invention, for the ratio of the number of reactive groups of compound (B) to the sum of the functions of compound (A) to be in the range from 0.1 to 0.8 and preferably from 0.3 to 0.8.

Compound (B) can thus correspond to any one of the formulae (B1) to (B3):

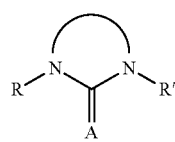

(B1)

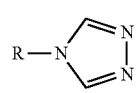

(B2)

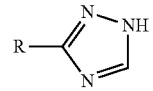

(B3)

where:

R denotes a unit containing at least one primary or secondary amine or alcohol group, R' denotes a hydrogen atom, A denotes an oxygen or sulphur atom or a group —NH, preferably an oxygen atom.

Preferred examples of compounds (B) are 2-aminoethylimidazolidone (UDETA), 1-(2-[(2-aminoethyl)amino] ethyl)imidazolidone (UTETA), 1-(2-[2-[(2-aminoethylamino]ethyl)amino)ethyl]imidazolidone (UTEPA), 3-amino-1,2,4-triazole and 4-amino-1,2,4-triazole.

As an example of a compound that can be obtained at the end of the first stage of the method described above, we may mention:

UDe 1008 resulting from reaction between Empol®1008 and UDETA;

UDe 1060 resulting from reaction between Unidyme® 60 and UDETA;

UDe 1060/1008 resulting from reaction between Empol®1008, Unidyme® 60 and UDETA;

UDe 1017 resulting from reaction between Pripol® 1017 and UDETA;

UDe 1048 resulting from reaction between Pripol® 1048 and UDETA;

UDe 1014 resulting from reaction between Unidyme® 14 and UDETA;

UDe 1040 resulting from reaction between Pripol® 1040 and UDETA;

UDe 0980 resulting from reaction between Radiacid® 0980 and UDETA.

Depending on the starting fatty acid, we obtain a compound that can be semi-crystalline with a melting point ($T_m$) most often between 30 and 150° C. and with a glass transition temperature ($T_g$) most often between −50° C. and 20° C.

This compound is then reacted, in the second stage of the method according to the invention, with a compound that is at least bifunctional (C), in such a way that the functions of (C) react with the second functions, i.e. the remaining reactive functions, of compound (A). In this stage it is necessary to avoid catalytic conditions that could lead to homopolymerization of compound (C).

Compound (C) has at least two functions, identical or different, selected notably from the epoxy, alcohol and amine functions.

Compound (C) is preferably a diepoxide. It can thus be selected from: bisphenol A diglycidyl ether, bisphenol F diglycidyl ether, tetrabromo bisphenol A diglycidyl ether, or hydroquinone diglycidyl ether, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, neopentylglycol diglycidyl ether, bisphenol A polyethylene glycol diglycidyl ether, bisphenol A polypropylene glycol diglycidyl ether, diglycidyl ester of terephthalic acid, polyunsaturated epoxidized fatty acids, and epoxidized limonene; and mixtures thereof.

In a variant, compound (C) can be a polyepoxide containing at least three epoxide functions, selected for example from: triglycidyl ether of castor oil, 1,1,1-tris(hydroxymethyl)propane triglycidyl ether, trisphenol triglycidyl ether, glycerol triglycidyl ether, glycerol propoxylate triglycidyl ether, glycerol ethoxylate triglycidyl ether, trimethylol propane triglycidyl ether, sorbitol polyglycidyl ether, polyglycerol polyglycidyl ether, pentaerythritolpolyglycidyl ether, poly(glycidyl acrylate), polyglycidyl methacrylate, polyunsaturated epoxidized fatty acids, epoxidized vegetable oils, epoxidized fish oils and epoxidized limonene.

In yet another variant, compound (C) can be a diol. In this case, compound (C) can be selected from: ethylene glycol, propylene glycol, tetramethylene glycol, hexamethylene glycol, octanediol, nonanediol, decanediol, diethylene glycol, dipropylene glycol, triethylene glycol, tetraethylene glycol, polyethylene glycol, polypropylene glycol, polytetramethylene glycol, polyesters with hydroxy ends, polybutadienes with hydroxy ends, polydimethylsiloxanes with hydroxy ends, polyisobutylenes with hydroxy ends, polybutadiene-co-acrylonitrile copolymers with hydroxy ends, diol dimers obtained from fatty acids and mixtures thereof.

According to another possibility, compound (C) can be a polyol containing at least three alcohol functions. Examples of such compounds are notably: sugars such as sorbitol, pentaerythritol, trimethylolpropane, as well as glycerol and its ethoxylated and propoxylated derivatives, castor oil and diol dimers obtained from fatty acids such as Pripol 2033 from Uniqema.

It is understood that the material according to the invention contains bonding bridges, preferably amide, formed in the first stage of its synthetic process, by reaction of the reactive groups (advantageously primary or secondary amine) of compound (B) with reactive functions, called "first functions" (advantageously, acid functions), of compound (A) and of the bonding bridges (advantageously ester), formed in the second stage of this process, by reaction of the reactive functions (preferably acid) that remain, called "second functions", of compound (A) with reactive functions (advantageously epoxy) of compound (C). This material also contains hydrogen bonds between the associative groups carried by the molecules from which it is constituted. The presence of these reversible hydrogen bonds, which can be broken by a temperature rise and can re-form at room temperature, enables the material according to the invention to have low viscosity in the molten state, facilitating its application, and optionally a high elongation at break at room temperature, yet without having a high molecular weight.

The dendritic molecules constituting said material contain a soluble fraction, as well as optionally an insoluble fraction, i.e. a fraction representing from 0.1 to 90% of the weight of the material and which is not soluble in any proportions in any solvent. The number-average molecular weight of the soluble fraction is preferably between 300 and 300 000 g/mol, as measured by GPC.

According to one embodiment of the invention, the average number of associative end groups per molecule is at least 1.2, preferably at least 2, and even at least 2.2.

Moreover, it is understood that this material can contain molecules other than the dendritic molecules described previously, especially in the case when compound (A) contains trimers of fatty acids mixed with monomers and/or dimers of fatty acids. Advantageously, the material according to the invention contains at least 25% and, better still, at least 50% by number of said dendritic molecules.

It is preferred, according to the invention, that this material should also contain hydrophobic intermolecular bonds, advantageously due to interactions between alkyl groups carried by each of the dendritic molecules described previously. By "alkyl", we mean, in the sense of the invention, side groups ($C_nH_{2n+1}$) and not alkylene chains ($C_nH_{2n}$), for example. Especially preferably, each of these molecules contains $C_6$-$C_{24}$ alkyl chains, advantageously in greater number than said associative end groups. They can notably be supplied by compounds (A), especially in the case of trimers of fatty acids.

Compounds (A), (B) and (C) described previously can be introduced, in the method according to the invention, in the molten state or via a solvent.

The proportions of (A), (B) and (C) used in the method according to the invention determine the mechanical characteristics of the material according to the invention.

The material according to the invention advantageously displays elastomeric properties, i.e. the property that it can be submitted to uniaxial deformation at room temperature and can recover its initial dimension once this stress is removed, with a permanent strain less than 5% of its initial dimension.

It is preferable, moreover, for the material according to the invention to display properties of self-repair. We mean by this the capacity of the material, after elongation as far as rupture, followed by bringing the faces of the material where rupture occurred, into contact at room temperature, of reuniting and of being able to be submitted to tension again.

As mentioned above, the proportions, and the nature of (A), (B) and (C) used in the method according to the invention determine the mechanical characteristics of the material according to the invention.

Consequently, it is preferable for the material according to the invention to be such that:

compound (A) is a trimer of at least one of the following acids: undecylenic acid, myristoleic acid, palmitoleic acid, oleic acid, linoleic acid, linolenic acid, ricinoleic acid, eicosenoic acid, docosenoic acid, eicosapentaenoic acid and docosahexaenoic acid.

compound (B) is selected from: 2-aminoethylimidazoline (UDETA), 1-(2-[(2-aminoethyl)amino]ethyl)imidazolidone (UTETA), 1-(2-[2-[(2-aminoethylamino]ethyl)amino)ethyl]imidazolidone (UTEPA), 3-amino-1,2,4-triazole and 4-amino-1,2,4-triazole, and compound (C) is selected from: bisphenol A diglycidyl ether, bisphenol F diglycidyl ether, tetrabromo bisphenol A diglycidyl ether, hydroquinone diglycidyl ether, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, neopentylglycol diglycidyl ether, bisphenol A polyethylene glycol diglycidyl ether, bisphenol A polypropylene glycol diglycidyl ether, diglycidyl ester of terephthalic acid, polyunsaturated epoxidized fatty acids, epoxidized limonene and mixtures thereof; or from triglycidyl ether of castor oil, 1,1,1-tris(hydroxymethyl)propane triglycidyl ether, trisphenol triglycidyl ether, glycerol triglycidyl ether, glycerol propoxylate triglycidyl ether, glycerol ethoxylate triglycidyl ether, trimethylol propane triglycidyl ether, sorbitol polyglycidyl ether, polyglycerol polyglycidyl ether, pentaerythritolpolyglycidyl ether, poly(glycidyl acrylate), polyglycidyl methacrylate, polyunsaturated epoxidized fatty acids, epoxidized vegetable oils, epoxidized fish oils, epoxidized limonene and mixtures thereof.

The material, in particular the "self-repairing" material, according to the invention can notably be used for making seals, watch straps, thermal or acoustic insulation, tyres, rubber bands, cables, cladding, soles of footwear, packaging, coatings (paints, films, cosmetics, sealing coatings), patches (cosmetic or dermo-pharmaceutical) or other systems for trapping and release of actives, wound dressings, flexible hose clips, vacuum tubes, pipes and hoses for conveying fluids, and generally components requiring good resistance to tearing and/or to fatigue, and for which properties of self-repair are required, or additives for hot-melt glues and adhesives.

The "self-repairing" material according to the invention can also be used for making novel shapes, for example for making O-ring or flat seals, notably by abutment of the two ends of a straight tube, plate, cylinder or lamina.

The invention therefore also relates to the use of the material according to the invention for the aforementioned purposes.

In these applications, the material according to the invention can be used as such or in single-phase or multi-phase mixtures, with one or more compounds such as petroleum fractions, solvents, mineral and organic fillers, plasticizers, tackifying resins, antioxidants, pigments and/or colorants, for example, in emulsions, suspensions or solutions. It will moreover be advantageous to add talc to the material obtained according to the invention (obtained from stage (b) of the method described previously), for example by dusting, in order to facilitate its handling and possibly removal from the mould when it is intended to be formed in a mould.

In a variant, this material can be used, for the manufacture of a cosmetic composition usually containing a physiologically acceptable medium, i.e. compatible with keratinous substances.

The present invention therefore also relates to such a cosmetic composition containing the material described previously as well as optionally at least one oil and/or water and/or an alcohol.

In addition it relates to the use of said cosmetic composition for the care and/or make-up of the skin and/or its appendages (such as the eyelashes and the nails) and/or of the lips or for the washing, conditioning and/or dressing of the hair.

The invention will be better understood from the following examples, given for purposes of illustration only and not intending to restrict the scope of the invention, defined by the appended claims.

EXAMPLE

Example 1

Preparation of a Material According to the Invention

A 4-liter glass reactor equipped with a mechanical stirrer, a temperature sensor, feed of nitrogen via a plunger tube, a pouring funnel, a Dean-Stark surmounted by a condenser and a flask heater, was charged with 1300 g of a trimer of fatty acids (Pripol® 1040, acid number=188 (mg of KOH/g), i.e. 4.36 mol of acid functions). 299 g of 2-aminoethyl-imidazolinone (UDETA, alkalinity index=7.3 meq/g or 2.18 mol, 0.5 equivalent) in the molten state, was introduced into the pouring funnel. The reactor was heated to 80° C., then while stirring and under a nitrogen stream, the UDETA was poured for a period of 10 minutes. The temperature was raised gradually to 180° C. over a period of 4 hours, then it was left to react for 2 hours at 180° C. The amount of water recovered was 39 g (2.18 mol). It was left to cool to 130° C., recovering 1475 g of a brown viscous liquid, which solidified at room temperature. The acid number (mg KOH/g of product required to neutralize the acids groups) of the product obtained was 67.5 mg of KOH/g.

7.5 g of this product was then put in a PTFE beaker of diameter 5 cm, with 1.73 g of Araldite® LY556 (epoxy prepolymer DGEBA with average number of hydroxyl groups per molecule n=0.15 or a number-average molecular weight Mn=382.6). After heating the beaker to 150° C., the mixture was homogenized, using a spatula and then poured into a PTFE mould of diameter 8 cm, held at 150° C. for 1 hour and then at 125° C. for 48 hours. The mould was then cooled to room temperature. After removal from the mould, we obtained a flexible film of material called RH-4, with thickness of about 1 mm at the centre. After cutting with a razor blade, it was found that this film repaired itself spontaneously when the pieces were brought back in contact in less than one hour.

Example 2

Preparation of a Material According to the Invention

The procedure was the same as in Example 1, using 1625 g of Pripol® 1040 (acid number-188 mg of KOH/g, or 5.46 mol of acid functions) and 224.4 g of UDETA (1.64 mol, 0.3 equivalent). We recovered 26.5 g of water (1.64 mol) and 1770 g of a brown viscous liquid which solidified at room temperature. The acid number of the product was 105.8 mg of KOH/g.

7.75 g of this product was then put in a PTFE mould of diameter 8 cm, with 2.8 g of Araldite® LY556. After heating the mould to 150° C., the mixture was homogenized using a spatula, held at 150° C. for 1 hour and then at 125° C. for 48 hours. The mould was then cooled to room temperature. After removal from the mould, we obtained a flexible film having a thickness of about 1.5 mm at the centre. After cutting with a razor blade, it was found that this film repaired itself spontaneously when the pieces were brought back in contact in less than one hour.

Example 3

Preparation of a Material According to the Invention 5.62 g of dimer/trimer mixture of acid Unidyme® 60 and 1.40 g of 2-aminoethylimidazolidinone (UDETA) of molar purity greater than 95% were poured into a 50-ml three-necked flask equipped with a heating magnetic stirrer, feed of gas and a connecting pipe for vacuuming. The mixture was heated, under a stream of nitrogen, at 180° C. for 12 hours. Regularly, a light vacuum was applied with a water-jet pump in order to remove the water that was dissolved in the medium. The liquid mixture was cooled to 150° C., then 1.91 g of epoxy resin Araldite® LY556 was added. After 45 min of rest at 150° C., the mixture was poured into a PTFE mould of diameter 8 cm and put in a stove at 125° C. for 48 hours.

The sample obtained after removal from the mould was in the form of a flexible film with thickness of 1.6 mm.

Example 4

Mechanical Testing

Dumb-bell shaped test specimens with the following dimensions: overall length: 35 mm, overall width: 6.5 mm, length of the central zone: 10 mm, width of the central zone: 2 mm, thickness: 1.6 mm, were obtained from the film obtained from Example 3 by punching with a punch.

Tensile tests were carried out at 25° C. using the Instron® tensile tester, equipped with a 10 N force meter, at a speed of 2 mm/min. The following results were obtained:

Deformation at break: 427%
Breaking stress: 0.65 MPa

Using the same machine, a creep test was carried out at 25° C. as follows: the test specimen was marked with two lines on either side of the central zone, the image of the test specimen was recorded using a scanner with a resolution of 600 dpi and the distance between the two lines was measured on the image, then the test specimen was submitted to elongation at a speed of 2 mm/min to deformation of 200%. Then the deformation of 200% was maintained for 1 hour. After that, the test specimen was removed from the jaws and then left at rest for 12 hours at 25° C. The distance between the two lines was then measured again in the same way as previously.

Distance between lines before elongation: 12.5 mm
Distance between lines after elongation: 12.9 mm, i.e. a permanent strain of 3%.

Tests of self-repair at 25° C. were carried out as follows: the test specimen was first cut in its centre using a razor blade. After a time t1, the two surfaces were brought back in contact manually. It was found that they adhered to one another immediately. The test specimen was then left at rest for a time t2. After that, a tensile test to rupture was carried out in the conditions mentioned above.

The following results were recorded:

| Specimen | t1 (min) | t2 (min) | Maximum stress before rupture (MPa) | Elongation at break (%) |
|---|---|---|---|---|
| 1 | 10 | 1 | 0.10 | 189 |
| 2 | 10 | 3 | 0.16 | 234 |
| 3 | 10 | 14 | 0.19 | 280 |

This example shows that after self-repair, the sample was again able to withstand considerable deformation before rupture. This example also shows that the quality of the self-repair improves as the time t2 increases.

Example 5 (Comparative)

Synthesis and Mechanical Properties of a Material 3.82 g of epoxy resin Araldite® LY556+5.60 g of trimer of acid Unidyme® 60 were put in a 100-mL flask equipped with a magnetic stirrer and a heating bath. The mixture was heated to 160° C. with stirring until it became miscible, then it was poured into a PTFE mould of diameter 80 mm and finally put in a stove at 125° C. for 48 hours. A flexible film, with a thickness of about 1.35 mm was obtained. Infrared spectroscopy showed:

disappearance of the band $v_{C=O}$ of the acid at 1707 cm$^{-1}$
disappearance of the band $v_a$ of the epoxy at 914 cm$^{-1}$
appearance of the band $v_{C=O}$ of the ester at 1736 cm$^{-1}$ Mechanical tests were performed, on this film in the same conditions as previously.

The tensile test gave the following results:
Elongation at break: 195%
Breaking stress: 5.5 MPa A test of self-repair at 25° C. was carried out in the same way as in Example 4.

With the times $t_1$=10 minutes and $t_2$=3 hours, the following results were recorded:
Elongation at break: 5.1%
Maximum stress before rupture: 0.07 MPa.

This example shows that the property of self-repair is not observed in the case oil a network made up of chemically crosslinked macromolecules but without intermolecular hydrogen bonds.

Example 6

Synthesis and Mechanical Properties of a Material According to the Invention 150 g of Pripol® 1040 (from Uniqema, acid number=188, i.e. 0.504 mol of acid functions) was put in a 500 ml Schott reactor, equipped with a mechanical stirrer, a condenser, a Dean-Stark, nitrogen feed, a pouring funnel and a temperature sensor. After heating to 80° C., 36.5 g of UDETA (from Arkema, alkalinity index=6.9 meq/g, i.e. 0.252 mol of amine functions) was introduced via the pouring funnel. After heating at 160° C. for 5 hours under a nitrogen stream, the water formed was removed in the Dean-Stark. We then allowed the temperature to decrease to 145° C., and added 62.9 g of epoxidized soya oil (Ecepox PB1, from Arkema, epoxide number=4 mmol/g, i.e. 0.252 mol of epoxide functions) and it was left to react for 15 minutes at 145-150° C. The reaction mixture was poured into a Teflon® tray, which was put in a stove at 120° C. for 40 hours.

The product thus obtained was dusted with talc for easier handling and removal from the tray. Once the product was removed from the tray, the other surface (that in contact with the tray) was also dusted with talc. Strips 8 cm long by 1 cm wide and 2 mm thick were cut out for performing the mechanical tests. Pencil marks 4 cm apart were made on the specimen (2 cm on either side of the lengthwise centre). The specimen was then deformed manually until the marks were 14 cm apart, which corresponded to a deformation of 250%. The specimen was put on a table and its spring-back was observed. 5 minutes after releasing the specimen, the distance between the marks had returned to 4.2 cm. Half an hour later, the specimen had completely recovered its original dimensions and the distance between the marks was again 4 cm, which corresponded to 0% of residual deformation.

This example illustrates the elastomeric properties of the materials according to the invention.

The invention claimed is:

1. A material comprising talc and branched molecules whose backbone has at least two branchings, wherein each molecule is constituted of fragments that are at least bifunctional, obtained from compounds (C) containing at least two functions, identical or different, and of fragments that are at least trifunctional, obtained from compounds (A) containing at least three functions, identical or different, such that these fragments are joined together by ester bridges formed on each end of the bifunctional fragments, said bridges being formed by reacting one function from compound (C) with one function from compound (A), said molecules containing moreover, on the at least trifunctional fragments located at the ends of the branches, associative end groups capable of forming associations with one another by hydrogen bonds, wherein said associative end groups are connected to the trifunctional fragments via a direct bond or via a chain, wherein said associative end groups are obtained by reacting compounds (B) bearing each at least one of such associative end groups with functions of compound (A) that have not been involved in the formation of said ester bridges, wherein the associative end groups are selected from the imidazolidonyl, triazolyl, triazinyl, bis-ureyl, and ureido-pyrimidyl groups;
  wherein the material contains at least 25% by number of said branched molecules, and
  wherein said branched molecules each have $C_6$-$C_{24}$ alkyl chains.

2. The material according to claim 1, wherein a fraction of the branched molecules is insoluble and a fraction of the branched molecules is soluble.

3. The material according to claim 2, wherein the soluble fraction of said branched molecules has a number-average molecular weight between 300 and 300 000 g/mol.

4. Material according to claim 1, which is obtained according to the method comprising the following successive stages:
  (a) reaction of at least one compound that is at least trifunctional (A) bearing each at least three reactive functions, which are identical or different, including a first function and a second function, which are identical or different, with compounds (B) bearing each, on the one hand, at least one reactive group capable of reacting with the first functions of (A) and, on the other hand, at least one of said associative end groups;
  (b) reaction of the compound or compounds obtained in stage (a) with at least one compound that is at least bifunctional (C) containing functions, which are identical or different, and that are capable of reacting with the second functions of compound (A) to form ester bridges; and
  (c) addition of talc to the material obtained from stage (b).

5. The material according to claim 4, wherein:
  compound (A) contains at least three functions, identical or different, selected from the acid, ester or acyl chloride functions,
  compound (B) contains at least one reactive group selected from the primary or secondary amine or alcohol groups, and
  compound (C) contains at least two functions, identical or different, selected from the epoxy functions and alcohol functions.

6. The material according to claim 4, wherein compound (A) contains from 5 to 100 carbon atoms.

7. The material according to claim 4, wherein compound (A) is a trimer of fatty acid of vegetable origin.

8. The material according to claim 4, wherein compound (B) corresponds to formula (B1), (B2) or (B3):

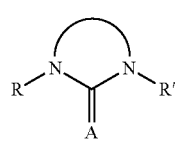
(B1)

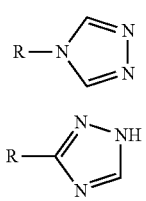
(B2)

(B3)

where:
  R denotes a unit containing at least one primary or secondary amine or alcohol group,
  R' denotes a hydrogen atom,
  A denotes an oxygen.

9. The material according to claim 8, wherein compound (B) is selected from the group consisting of 2-aminoethylimidazolidone (UDETA), 1-(2-[(2-aminoethyl)amino]ethyl) imidazolidone (UTETA), 1-(2-{2-[2-aminoethylamino] ethyl}amino)ethyl]imidazolidone (UTEPA), 3-amino-1,2,4-triazole and 4-amino-1,2,4-triazole.

10. The material according to claim 4, wherein compound (C) is a diepoxide.

11. The material according to claim 10, wherein compound (C) is selected from the group consisting of bisphenol A diglycidyl ether, bisphenol F diglycidyl ether, tetrabromo bisphenol A diglycidyl ether, hydroquinone diglycidyl ether, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, bisphenol A polyethylene glycol diglycidyl ether, bisphenol A polypropylene glycol diglycidyl ether, diglycidyl ester of terephthalic acid, polyunsaturated epoxidized fatty acids, and epoxidized limonene; and mixtures thereof.

12. The material according to claim 4, wherein compound (C) is a diol.

13. The material according to claim 12, wherein compound (C) is selected from the group consisting of ethylene glycol, propylene glycol, tetramethylene glycol, hexamethylene glycol, octanediol, nonanediol, decanediol, diethylene glycol, dipropylene glycol, triethylene glycol, tetraethylene glycol, polyethylene glycol, polypropylene glycol, polytetramethylene glycol, polyesters with hydroxy ends, polybutadienes with hydroxy ends, polydimethylsiloxanes with hydroxy ends, polyisobutylenes with hydroxy ends, polybutadiene-co-acrylonitrile copolymers with hydroxy ends, diol dimers obtained from fatty acids and mixtures thereof.

14. The material according to claim 4, wherein the ratio by number of the reactive groups of compound (B) to the sum of the first functions of compound (A) is in the range from 0.1:1 to 0.8:1.

15. The material according to claim 14, wherein the ratio by number of the reactive groups of compound (B) to the sum of the first functions of compound (A) is in the range from 0.3:1 to 0.8:1.

16. The material according to claim 4, wherein compound (A) contains from 24 to 90 carbon atoms.

17. The material according to claim 1, wherein compound (A) is a trimer of at least one of the acids selected from the group consisting of undecylenic, myristoleic, palmitoleic, oleic, linoleic, linolenic, ricinoleic, eicosenoic, docosenoic, eicosapentaenoic and docosahexaenoic acid.

18. A method of preparation of a material according to claim 1 comprising the following successive stages:
  (a) reacting compounds that are at least trifunctional (A) bearing each at least three reactive functions, which are identical or different, including a first and a second group of functions, which are identical or different, with compounds (B) bearing each, on the one hand, at least one reactive group capable of reacting with the first group of functions of (A) and, on the other hand, at least one of said associative end groups;

(b) reacting a compound or compounds obtained in stage (a) with compounds that are at least bifunctional (C) containing functions, which are identical or different, and that are capable of reacting with the second group of functions of (A) to form ester bridges.

19. A method for making seals, watch straps, thermal or acoustic insulation, tyres, rubber bands, cables, cladding, soles of footwear, packaging, coatings patches or other systems for trapping and release of actives, wound dressings, flexible hose clips, vacuum tubes, pipes and hoses for conveying fluids, additives for hot-melt glues and adhesives, and O-ring or flat seals, comprising mixing the material of claim 1, in single-phase or multi-phase mixtures, with one or more compounds selected from the group consisting of petroleum fractions, solvents, mineral and organic fillers, plasticizers, tackifying resins, antioxidants, pigments and colorants.

20. A cosmetic composition containing a material comprising branched molecules whose backbone has at least two branchings, wherein each molecule is constituted of fragments that are at least bifunctional, obtained from compounds (C) containing at least two functions, identical or different, and of fragments that are at least trifunctional, obtained from compounds (A) containing at least three functions, identical or different, such that these fragments are joined together by ester bridges formed on each end of the bifunctional fragments, said bridges being formed by reacting one function from compound (C) with one function from compound (A), said molecules containing moreover, on the at least trifunctional fragments located at the ends of the branches, associative end groups capable of forming associations with one another by hydrogen bonds, wherein said associative end groups are connected to the trifunctional fragments via a direct bond or via a chain, wherein said associative end groups are obtained by reacting compounds (B) bearing each at least one of such associative end groups with functions of compound (A) that have not been involved in the formation of said ester bridges, wherein the associative end groups are selected from the imidazolidonyl, triazolyl, triazinyl, bis-ureyl, and ureido-pyrimidyl groups;

wherein the material contains at least 25% by number of said branched molecules, wherein said branched molecules each have $C_6$-$C_{24}$ alkyl chains, and wherein the cosmetic composition additionally contains optionally at least one oil and/or water and/or an alcohol.

21. The cosmetic composition according to claim 20 for the care of and/or make-up for the skin, hair, nails or lips.

22. The cosmetic composition according to claim 20 for the washing and/or dressing of the hair.

* * * * *